(12) United States Patent
Menchen et al.

(10) Patent No.: US 10,941,439 B2
(45) Date of Patent: *Mar. 9, 2021

(54) SUBSTRATES AND METHODS USEFUL IN SEQUENCING

(71) Applicant: LIFE TECHNOLOGIES CORPORATION, Carlsbad, CA (US)

(72) Inventors: Steven M. Menchen, Fremont, CA (US); Guobing Xiang, Hayward, CA (US); Prasanna Thwar, San Jose, CA (US); Jeffrey Frediani, San Mateo, CA (US); Allen Wong, San Francisco, CA (US); Alfred Lui, Sunnyvale, CA (US); Lily Lu, Foster City, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/176,231

(22) Filed: Oct. 31, 2018

(65) Prior Publication Data

US 2019/0062807 A1 Feb. 28, 2019

Related U.S. Application Data

(63) Continuation of application No. 15/202,487, filed on Jul. 5, 2016, now Pat. No. 10,150,992.

(60) Provisional application No. 62/189,019, filed on Jul. 6, 2015.

(51) Int. Cl.
*C12Q 1/6834* (2018.01)
*C12Q 1/686* (2018.01)
*C12Q 1/6874* (2018.01)

(52) U.S. Cl.
CPC .......... *C12Q 1/686* (2013.01); *C12Q 1/6834* (2013.01); *C12Q 1/6874* (2013.01)

(58) Field of Classification Search
CPC ..... C12Q 1/686; C12Q 1/6834; C12Q 1/6874
See application file for complete search history.

(56) References Cited

U.S. PATENT DOCUMENTS

| | | | |
|---|---|---|---|
| 4,451,613 A | 5/1984 | Rousseau et al. |
| 4,507,382 A | 3/1985 | Rousseau et al. |
| 4,507,497 A | 3/1985 | Reilly et al. |
| 5,281,698 A | 1/1994 | Nitecki |
| 5,387,510 A | 2/1995 | Wu |
| 5,512,439 A | 4/1996 | Hornes et al. |
| 5,677,373 A | 10/1997 | Berge et al. |
| 6,242,235 B1 | 6/2001 | Shultz et al. |
| 6,525,183 B2 | 2/2003 | Vinayak et al. |
| 7,217,762 B1 | 5/2007 | Joergedal et al. |
| 9,139,667 B2 | 9/2015 | Menchen et al. |
| 9,243,085 B2 | 1/2016 | Fonnum et al. |
| 9,938,577 B2 | 4/2018 | Fonnum et al. |
| 10,144,968 B2 | 12/2018 | Fonnum et al. |
| 10,150,992 B2 | 12/2018 | Menchen et al. |
| 2004/0014080 A1 | 1/2004 | Tanga et al. |
| 2004/0203040 A1 | 10/2004 | Okada |
| 2004/0215011 A1 | 10/2004 | Deggerdal et al. |
| 2005/0014001 A1 | 1/2005 | Fonnum et al. |
| 2006/0131542 A1 | 6/2006 | Weng et al. |
| 2007/0299249 A1 | 12/2007 | Songe et al. |
| 2008/0139399 A1 | 6/2008 | Fonnum et al. |
| 2009/0026082 A1 | 1/2009 | Rothberg et al. |
| 2009/0069554 A1 | 3/2009 | Finne et al. |
| 2009/0081371 A1 | 3/2009 | Minami et al. |
| 2009/0291506 A1 | 11/2009 | Fonnum et al. |
| 2010/0137143 A1 | 6/2010 | Rothberg et al. |
| 2010/0207051 A1 | 8/2010 | Fonnum et al. |
| 2010/0282617 A1 | 11/2010 | Rothberg et al. |
| 2010/0304982 A1 | 12/2010 | Hinz et al. |
| 2013/0210991 A1 | 8/2013 | Fonnum et al. |
| 2013/0211006 A1* | 8/2013 | Menchen ............. C12Q 1/6834 525/54.2 |

FOREIGN PATENT DOCUMENTS

| | | | |
|---|---|---|---|
| EP | 0512844 | | 11/1992 |
| EP | 1726661 | | 11/2006 |
| EP | 2224014 | * | 1/2010 |
| EP | 2224014 | | 9/2010 |
| JP | H05211899 | | 8/1993 |
| JP | 2002211954 | | 7/2002 |
| JP | 2004258026 | | 9/2004 |

(Continued)

OTHER PUBLICATIONS

Devor et al., "Strategies for Attaching Oligonucleotides to Solid Supports", Integrated DNA Technologies 2005, 2010, and 2011, US, Jan. 1, 2005, URL:https://www.idtdna.comjpagesjdocsjdefault-sourcejtechnical-reportsjstrategies-for-attaching-oligonucleotides-to v6-3-14-14.pdf?sfvrsn=2 [retrieved on Aug. 9, 2016].

Dong et al., "Effect of Secondary Structure on the Activity of Enzymes Suspended in Organic Solvents", *Archives of Biochemistry and Biophysics*, vol. 334, No. 2, Article No. 0472, 1996, 406-414.

EP17160771, Search Report, dated Sep. 14, 2017, 1-20.
EP17160771, Partial Search Report, dated Jul. 3, 2017, 1-19.

(Continued)

*Primary Examiner* — Narayan K Bhat

(57) ABSTRACT

A hydrogel network includes a hydrogel polymer having a coupling site, an oligonucleotide conjugated at a terminal end to the hydrogel polymer at the coupling site, and a functional moiety coupled between the terminal end of the oligonucleotide and the coupling site. Such a hydrogel network can be formed by a method including activating a coupling site of a substrate and binding a linker moiety coupled to a terminal end of an oligonucleotide to the activated coupling site, a functional moiety coupled between the terminal end of the oligonucleotide and the linker moiety.

12 Claims, 10 Drawing Sheets

(56) References Cited

FOREIGN PATENT DOCUMENTS

| | | |
|---|---|---|
| JP | 2007003439 | 1/2007 |
| JP | 2007508416 | 4/2007 |
| JP | 2009092651 | 4/2009 |
| JP | 2009516008 | 4/2009 |
| WO | WO-2002000600 | 1/2002 |
| WO | WO-2002072791 | 9/2002 |
| WO | WO-2003084982 | 10/2003 |
| WO | WO-2003091392 | 11/2003 |
| WO | WO-2004086046 | 10/2004 |
| WO | WO-2005017180 | 2/2005 |
| WO | WO-2005037902 | 4/2005 |
| WO | WO-2005074993 | 8/2005 |
| WO | WO-2006103094 | 10/2006 |
| WO | WO-2006125124 | 11/2006 |
| WO | WO-2007020041 | 2/2007 |
| WO | WO-2007040986 | 4/2007 |
| WO | WO-2008005675 | 1/2008 |
| WO | WO-2010125170 | 11/2010 |
| WO | WO-2011053940 | 5/2011 |
| WO | WO-2013119894 | 8/2013 |
| WO | WO-2013119936 | 8/2013 |
| WO | WO-2013119956 | 8/2013 |
| WO | WO-2017004559 | 1/2017 |
| WO | WO-2017007774 | 1/2017 |

OTHER PUBLICATIONS

Ghosh et al., "N, N'-disuccinimidyl carbonate: a useful reagent for alkoxycarbonylation of amines", Tetrahedron Letters, vol. 33, No. 20, May 12, 1992, 2781-2784.

Haginaka et al., "Separation of enantiomers on a chiral stationary phase based on ovoglycoprotein-I. Influences of the pore size of base silica materials and bound protein amounts on chiral resolution", Journal of Chromatography A, vol. 773, Nos. 1-2, Jun. 27, 85-91.

Ion Torrent Systems, "GO Club (Genaris Omics Club)", http://genaport.genaris.com/GOC_sequencer_post.php?eid=00006, 2010, 1-2.

Lee, "Solubility of Tetrabutylammonium Bromide in Benzene between 298.15 K and 323.15 K", Journal of Chemical & Engineering Data, vol. 47, No. 5, 2002, 1135-1139.

Li et al., "Enzyme-linked synthetic oligonucleotide probes: non-radioactive detection of enterotoxigenic Escherichia coli in faecal specimens", Nucleic Acids Research, vol. 15, No. 13, Jul. 10, 1987, 5275-5287.

Ling et al., "Polymer-bound cellulose phenylcarbamate derivatives as chiral stationary phases for enantioselective HPLC", Journal of Separation Science, vol. 26, 2003, 1337-1346.

Meyer et al., "Hydrophobic Ion Pairing: Altering the Solubility Properties of Biomolecules", Pharmaceutical Research, vol. 15, No. 2, 1998, 188-193.

Murakami et al, Hybrid Hydrogels to Which Single-Stranded (ss) DNA Probe Is Incorporated Can Recognize Specific ssDNA, 2005, Macromolecules, vol. 38, 2005, 1535-1537.

Nemat-Gorgani et al., "The Interaction of Phospholipid Membranes and Detergents with Glutamate Dehydrogenase", European Journal of Biochemistry, vol. 74, No. 1, Mar. 1977, 129-137.

Nimse et al: "Immobilization Techniques for Microarray: Challenges and Applications", Sensors, vol. 14, No. 12, Nov. 25, 2014, 22208-22229.

Ogura, et al., "A Novel Active Ester Synthesis Reagent", Tetrahedron Letters, vol. 49, Jan. 1, 1979, 4745-4746.

PCT/US2013/025352, International Preliminary Report on Patentability, dated Aug. 12, 2014, 1-11.

PCT/US2013/025352, International Search Report and Written Opinion, dated May 22, 2013, 1-18.

PCT/US2016/040767, International Preliminary Report on Patentability, dated Jan. 11, 2018, 1-9.

PCT/US2016/040767, International Search Report and Written Opinion, dated Oct. 11, 2016, 1-14.

PCT/US2016/041012, International Search Report and Written Opinion, dated Oct. 4, 2016, 2017, 1-10.

PCT/US2016/041012, International Preliminary Report on Patentability, dated Jan. 9, 2018, 1-6.

Peppas et al., "Hydrogels in Biology and Medicine: From Molecular Principles to Bionanotechnology", Advanced Materials, vol. 18, 2006, 1345-1360.

Poellmann et al., "Characterizing and Patterning Polyacrylamide Substrates Functionalized with N-Hydroxysuccinimide", Cellular and Molecular Bioengineering, vol. 6, No. 3, Sep. 2013, 299-309.

Powers et al., "Enhanced Solubility of Proteins and Peptides in Nonpolar Solvents Through Hydrophobic Ion Pairing", Biopolymers, vol. 33, No. 6, 1993, 927-932.

Tang et al., "Polymerizing immobilization of acrylamide-modified nucleic acids and its application", Biosensors and Bioelectronics, vol. 24, No. 7, Mar. 15, 2009, 1817-1824.

Wang et al., "Different EDC/NHS activation mechanisms between PAA and PMAA brushes and the following amidation reactions", Langmuir: The Acs Journal of Surfaces and Colloids, vol. 27, No. 19, Oct. 4, 2011, 12058-12068.

Wilchek et al., "improved method for preparing n-hydroxysuccinimide ester-containing polymers for affinity chromatography", Bioconjugate Chemistry, vol. 5, No. 5, Jan. 1, 1994, 491-492.

Xion et al, "Responsive ONA-Based Hydrogels and Their Applications", Macromolecular Rapid Communications, vol. 34, No. 16, Jul. 16, 2013, 1271-1283.

* cited by examiner

SUBSTRATES AND METHODS USEFUL IN SEQUENCING

CROSS-REFERENCE TO RELATED APPLICATION(S)

This application is a continuation of U.S. patent application Ser. No. 15/202,487, filed Jul. 5, 2016, which claims benefit of U.S. Provisional Application No. 62/189,019, filed Jul. 6, 2015, each of which is incorporated herein by reference in its entirety.

FIELD OF THE DISCLOSURE

This disclosure, in general relates to discrete polymer network substrates useful in sequencing and related applications, methods for making such discrete polymer networks, and methods for using such discrete polymer networks.

BACKGROUND

Genetic testing is of increasing interest to the medical and scientific communities. In medicine, genetic testing provides details regarding the origin of disease, susceptibility to ailments, responsiveness to drugs, and identification of inherited traits. Animal sciences look to genetic testing to provide similar details in addition to using genetic testing for classification of species and determining migration patterns, among other uses. In other fields, such as agricultural science, genetic testing is used to identify gene sequences that can be incorporate into strains of flora or fauna to reduce susceptibility to pests and disease and to improve production.

While many genetic testing techniques have been proposed, recent genetic testing techniques rely on discrete nucleic acid conjugated polymer networks disposed on a device, such as an optical device or an ion sensitive device that can be used to detect nucleotide incorporation, for example. In a particular example, the discrete conjugated networks can be deposited into wells disposed over ion sensitive field effect transistors, which measure pyrophosphate or hydrogen ions released as a result of nucleotide incorporation. Other techniques rely on arrays of discrete networks disposed on substrates without wells.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION

In an exemplary embodiment, a substrate can include an oligonucleotide or nucleic acid conjugated to the substrate at a coupling site. A moiety can be attached to a modified nucleotide incorporated in the oligonucleotide or nucleic acid. For example, the moiety can be attached to a nucleotide through a linkage to the base, where the linkage is attached at the 5-position of pyrimidine bases, such as thymidine and cytidine, or where the linkage is attached at the 7-position of 7-deaza-purine bases, such as guanosine and adenosine. The moiety can be attached to a modified nucleotide coupled at a terminal end of the oligonucleotide or nucleic acid or can be secured at any base position of that oligonucleotide or nucleic acid. In a particular example, the moiety is a dye moiety, such as a TAMRA dye or fluorescein dye. In another example, the functional moiety acts as a buffering agent.

In another example, a moiety can be attached to a non-nucleotide structure secured between the terminal end of the oligonucleotide or nucleic acid and the coupling site of the substrate. In an example, the substrate is a discrete substrate for example, including a hydrogel network, such as a polyacrylamide network. In a particular example, the dye moiety is coupled to a nucleotide analog at the terminal of the oligonucleotide or nucleic acid, for example, coupled between the terminal end of the oligonucleotide or nucleic acid and the coupling site.

In a further example, such a discrete substrate having the dye-modified oligonucleotide coupled to the coupling site finds particular use in preparing discrete substrates that include a clonal population of nucleic acids, and for example, can be used for sequencing or quantitative amplification.

Figure 1:
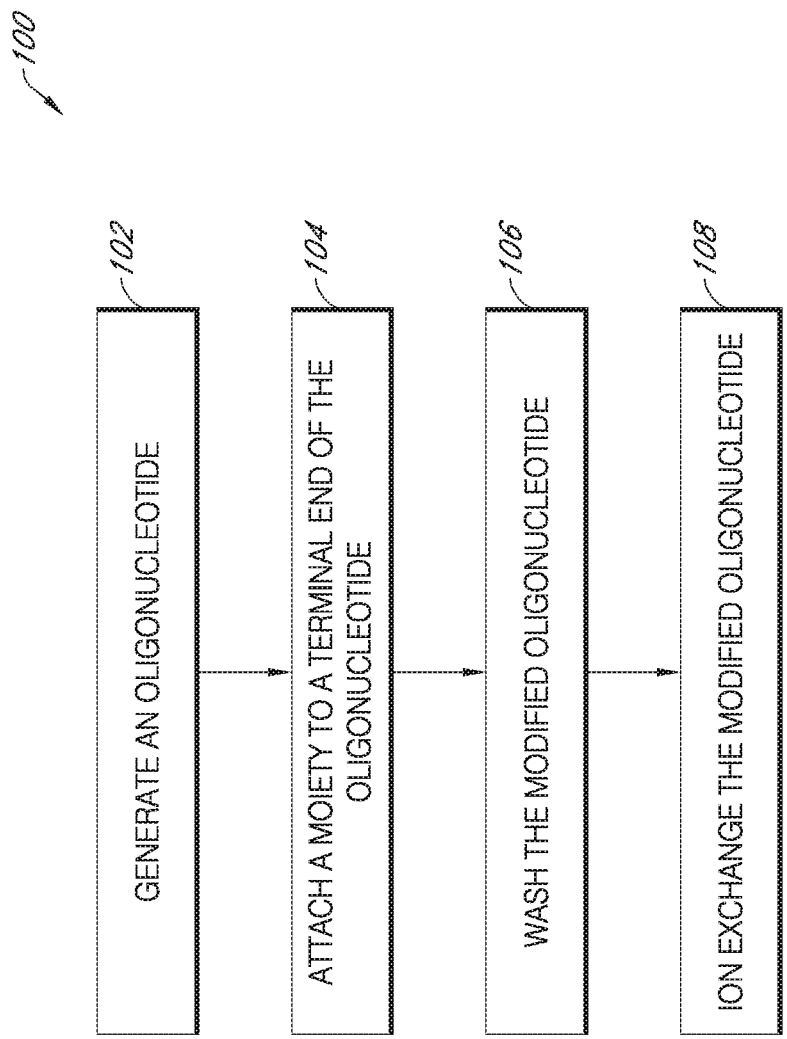
FIG. 1 includes a flow diagram illustrating an exemplary method for preparing an oligonucleotide.
Figure 2:
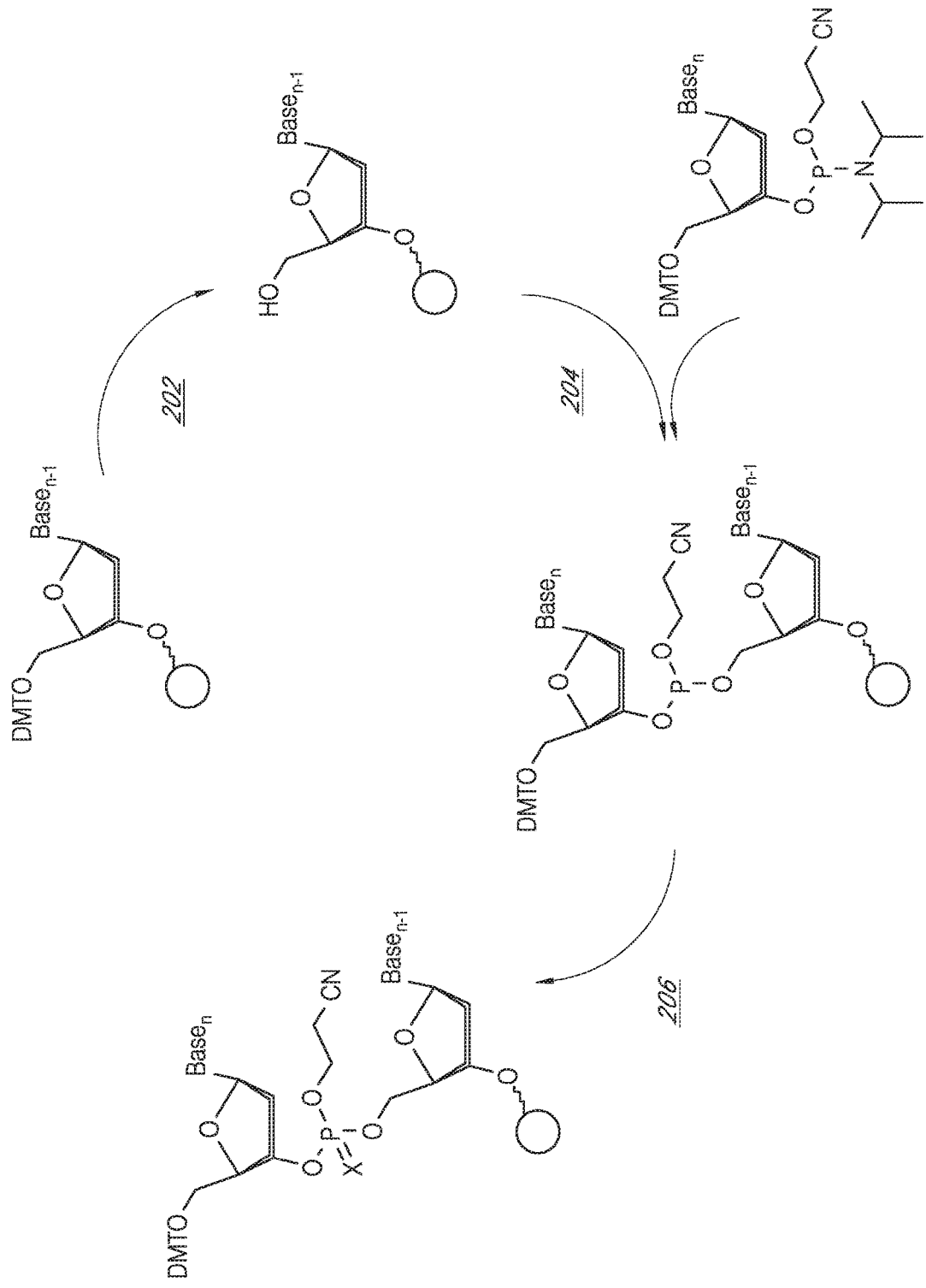
FIG. 2 illustrates an exemplary method for preparing an oligonucleotide.

In an exemplary embodiment illustrated in FIG. 1, a method 100 includes generating an oligonucleotide, as illustrated at 102. In a particular example, the oligonucleotide can be generated utilizing phosphoramidite chemistries and synthesized on a substrate. For example, as illustrated in FIG. 2, the terminal base of an oligonucleotide can be deprotected (202), for example, through detritylation to provide a 5' hydroxyl. A phosphoramidite-modified nucleotide can be added (204) to replace the 5' hydroxyl in the presence of an acidic azole catalyst, such as tetrazole, 2-ethylthiotetrazole, 2-benzylthiotetrazole, 4,5-dicyanoimidazole, or a combination thereof. The resulting phosphite can be oxidized (206) to a phosphate, and the process repeated. While the method of FIG. 2 illustrates a cyano ether modified phosphoramidite or a DMT protected 5' hydroxyl, other similar protective chemistries can be utilized in a process to generate an oligonucleotide.

A modified nucleotide including a functional moiety can be attached to a terminal end of the oligonucleotide or nucleic acid, as illustrated at 104. In particular, the modified nucleotide can be attached proximal to the 5' end of the oligonucleotide. In a particular example, the modified nucleotide can include a moiety coupled to a modified base and added to the 5'end of the oligonucleotide using similar phosphoramidite chemistry as described above.

An additional linker moiety can be coupled proximal to the terminal end of the oligonucleotide, such as attaching to the modified base to which the functional moiety is coupled. In a particular, example, the 5' hydroxyl of the modified nucleotide can be deprotected, and the linker moiety can be coupled to the deprotected 5' hydroxyl. In another example, the modified nucleotide can be secured at any base position within the oligonucleotide or nucleic acid. Alternatively, a non-nucleotide structure including the functional moiety can be secure to a terminal end of the oligonucleotide.

In a particular example, the functional moiety can be incorporated into the oligonucleotide either by the use of a labeled phosphoramidite, where the functional moiety is incorporated during the solid phase synthesis of the oligonucleotide. In another example, the moiety can be incorporated after deprotection and cleavage of the oligonucleotide from the solid phase support. For example, the moiety can be incorporated a point along the oligonucleotide structure at which a reactive group, such as a protected amine, is attached to the nucleotide phosphoramidite through a linkage at the 5-position of pyrimidine bases such as thymidine and cytidine, or where the linkage is attached at the 7-position of 7-deaza-purine bases, such as guanosine and adenosine. In an alternative example, the moiety can be incorporated at a protected amine incorporated into a non-nucleotide structure. After cleavage and deprotection of the oligonucleotide containing the deprotected reactive group, the oligonucleotide can be reacted with a reactive group attached to the functional moiety that is compatible with the reactive group on the oligonucleotide. For example, the reactive moiety can be an NHS ester of the functional moiety when the reactive group on the oligonucleotide is an amine.

Figure 3:
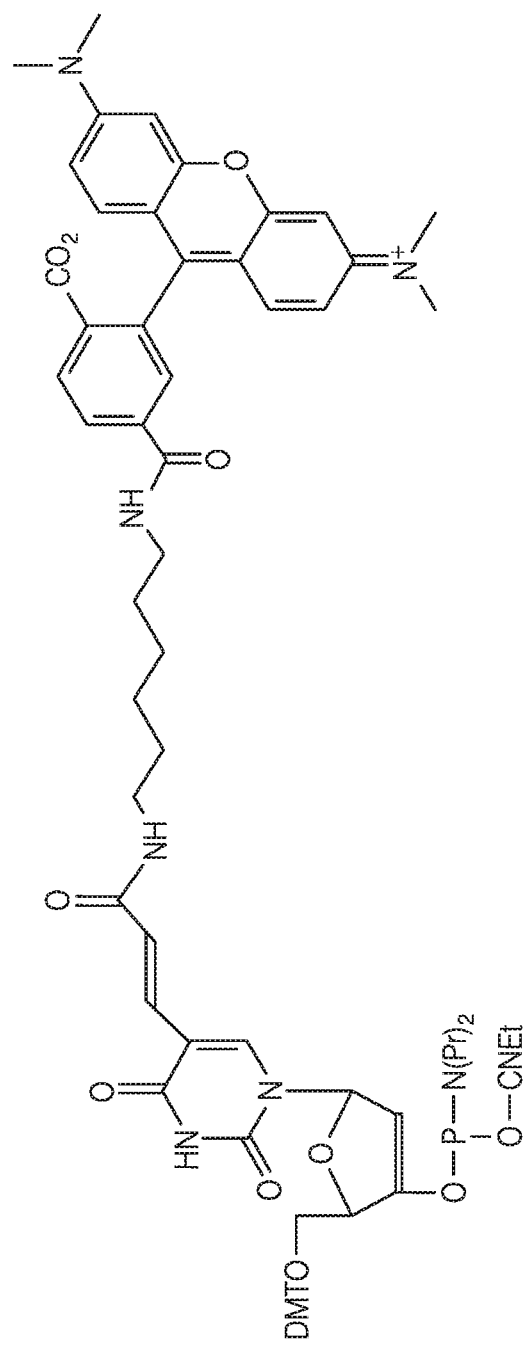
FIG. 3 and FIG. 4 include illustrations of exemplary dye-labeled nucleotides.

In an example, the functional moiety includes a dye moiety. For example, the dye moiety can be a rhodamine dye. In another example, the dye moiety can be a 5-carboxytetramethylrhodamine, tetramethylrhodamine (TAMRA) Alkyne, or variations thereof. For example, as illustrated in FIG. 3, a modified thymine or uridine nucleotide includes a coupled dye moiety. FIG. 3 illustrates an exemplary TAMRA dye moiety attached to a thymine phosphoramidite.

Figure 4:
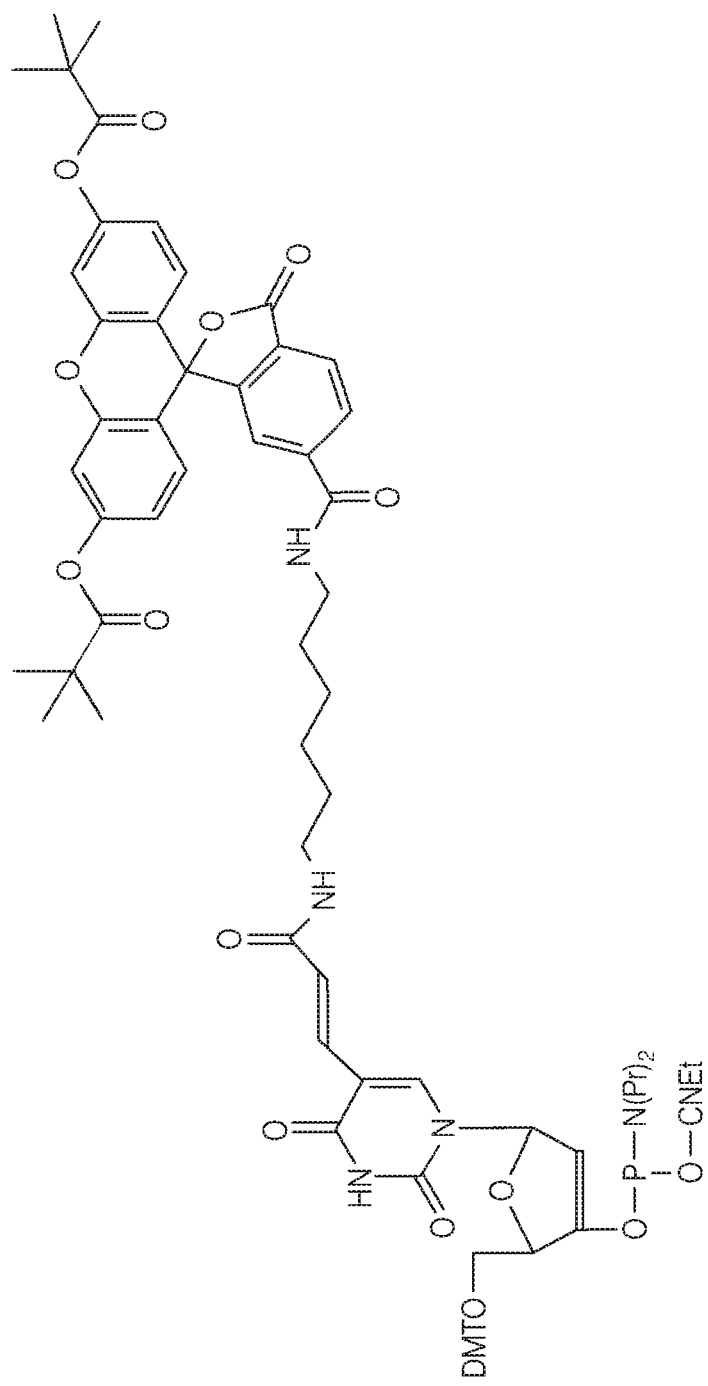

In another example, the dye moiety can be a fluorescein dye. For example, the fluorescein dye can be a dipivaloylfluorescein dye, such as a 5-dimethoxytrityloxy-5-[N-(3',6'-dipivaloylfluoresceinyl)-amino] dye. Exemplary dyes are Alexa Fluor® dyes. FIG. 4 illustrates an exemplary fluorescein-modified thymine nucleotide.

In an alternative example, the functional moiety can be a buffering moiety. An example buffering moiety can have a determinable pKa that can be covalently linked to or integrated with a nucleotide phosphoramidite or other phosphoramidite non-nucleotide structure. Examples of buffering moieties and their structures that may be linked or integrated as moieties include N-(3-morpholin-4-yl propyl, triethanolamine:

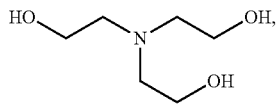

N-[tris(hydroxymethyl)methyl]-2-aminoethanesulfonic acid:

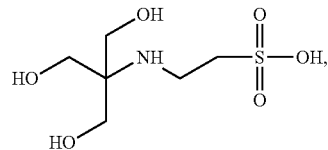 [SMILES: O=S(=O)(O)CCNC(CO)(CO)CO]

3-(N-tris[hydroxymethyl]methylamino)-2-hydroxypropanesulfonic acid:

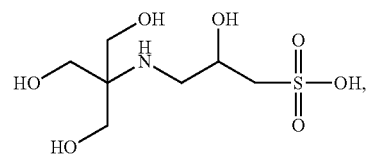 [SMILES: O=S(=O)(O)CC(O)CNC(CO)(CO)CO]

N-(2-hydroxyethyl)piperazine-N-(2-ethanesulfonic acid):

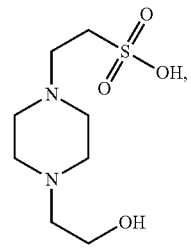 [SMILES: O=S(=O)(O)CCN1CCN(CCO)CC1]

N-(2-acetamido)-2-aminoethanesulfonic acid:

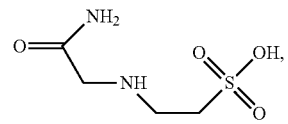 [SMILES: NC(=O)CNCCS(=O)(=O)O]

imidazole:

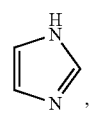

and
acetate:

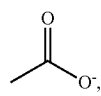

or any combination thereof.

Buffering moieties can also be chosen according to a predetermined pKa of the buffering moieties. For example, the predetermined pKa values of solution phase buffering groups may include a range of from about 4.5 to about 9.0, such as, for example, about 6.0 to about 8.0. By way of example only, the predetermined pKa values of the buffering groups may be chosen from about 4.76, about 6.8, about 6.9, about 7.5, about 7.6 and about 7.8.

Figure 5:
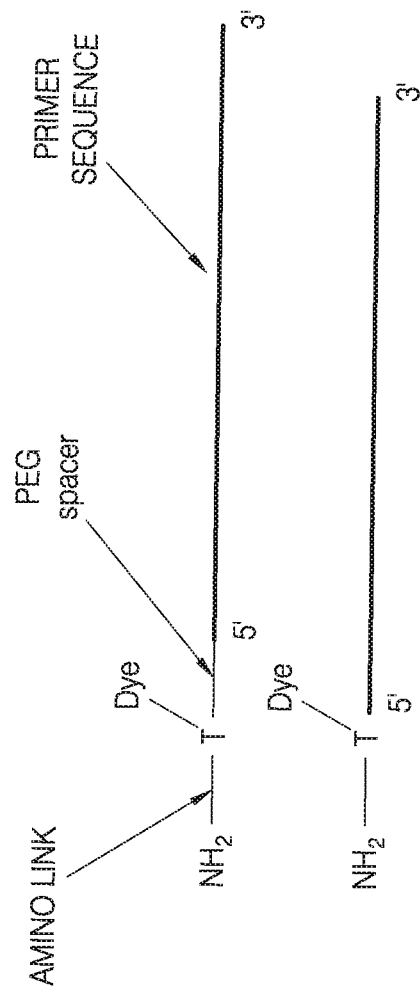
FIG. 5 includes illustrations of exemplary dye-labeled oligonucleotides.

Such modified phosphoramidite nucleotides can be incorporated at a terminal end of the oligonucleotide. In particular, as illustrated in FIG. 5, an oligonucleotide primer sequence can be attached to a dye modified nucleotide, such as a thymine nucleotide, and a reactive terminal group W can be attached by a linker to the modified nucleotide. Optionally, the terminal nucleotide of the oligonucleotide primer sequence can be modified with a polyethylene glycol (PEG) to which the subsequent die modified nucleotide is attached.

Returning to FIG. 1, following the formation of the dye-modified oligonucleotide, the oligonucleotide can be washed, as illustrated 106. For example, the oligonucleotide can be washed to remove reaction byproducts. In addition, protective moieties such as ester moieties (e.g. cyano ester moieties protecting an oxygen of the phosphate) can be removed using a base wash.

Further, the oligonucleotide can be subjected to an ion exchange, as illustrated at 108, to remove metal cations from association with the oligonucleotide and provide more lipophilic moieties that permit the oligonucleotide to preferentially stay in solution in nonaqueous solvents.

In a particular example, the biomolecule can be made more lipophilic by exchanging metal counter ions with cations, such as ammonium or phosphonium cations, having lipophilic moieties. In a particular example, an amine-terminated nucleic acid can undergo ion exchange prior to conjugation with the polymer substrate. In particular, metal ions associated with the nucleic acid can be replaced with lipophilic counter ions, as illustrated in FIG. 6.

Figure 6:
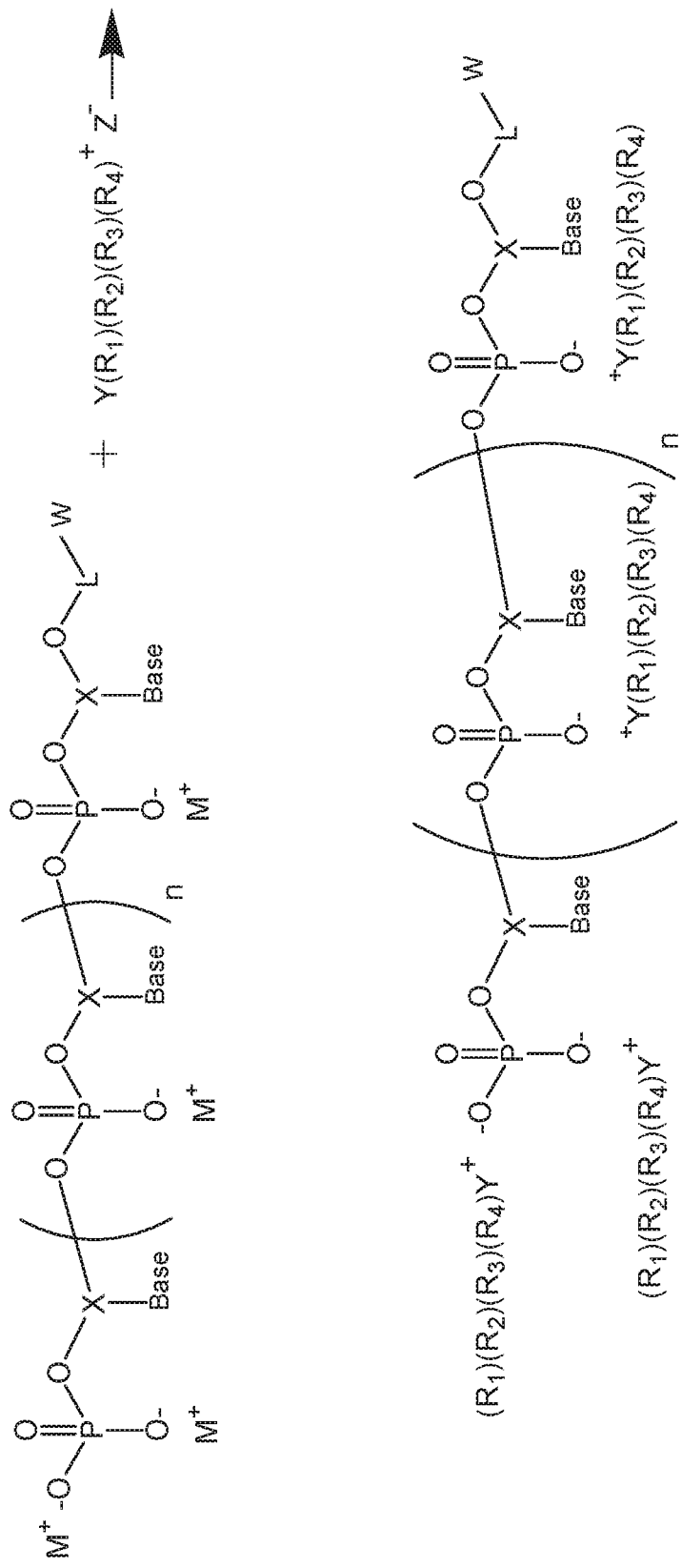
FIG. 6 includes an illustration of an exemplary method for preparing an oligonucleotide.

As illustrated in FIG. 6, counter ions (e.g., metal ions) of a biomolecule can be exchanged with lipophilic counter ions to provide a biomolecule complex that is more lipophilic. As used herein, lipophilic counter ions are ions that incorporate functionality (e.g., alkyl moieties) that, when the counter ion is associated with the biomolecule, shield ions of the biomolecule, rendering the biomolecule more lipophilic and able to dissolve in a non-aqueous solvent. For example, the illustrated biomolecule is a polynucleotide. As illustrated, the polynucleotide is formed of a plurality of polymerized nucleotides. The carbohydrate moiety (X) of a nucleotide is bound to a phosphate group of a neighboring nucleotide. Each phosphate group is associated with a cationic counter ion (M). In an example, the cationic counter ion (M) can be a metal ion. In another example, the cationic counter ion (M) can be ammonium or a proton. In addition, the polynucleotide can include a linker group (L), linking a reactive group (W) to the nucleotide chain. Alternatively, the biomolecule can be a polynucleotide analog having a similar linker/reactive group structure, and the polynucleotide can have the reactive group (W) extending from one or more of the bases in addition to or instead of from the carbohydrate (X).

In an example, the linker group (L) includes a hydrocarbon, an ether or polyether group, or a combination thereof. The reactive group (W) can function to react with functional groups formed on a substrate, such as a polymeric substrate. In a particular example, the reactive group (W) can be an amine, thiol, maleimide, acetylene, azide, or a combination thereof. For example, the reactive group (W) can be an amine or a thiol. In particular, the reactive group (W) can be an amine. In another example, the reactive group (W) can be a maleimide. In a further example, the reactive group (W) can be acetylene. In an additional example, the reactive group (W) can be an azide.

The polynucleotide is exposed to a lipophilic counter ion, such as a positively-charged counter ion having lipophilic moieties. The lipophilic counter ion can include a positively-charged member (Y) coupled to one or more hydrocarbon groups (R1, R2, R3, R4) and associated with an opposing ion (Z). In an example, the positively charged member (Y) can be nitrogen, phosphorus, sulfur, arsenic, or any combination thereof. In particular, the positively charged member (Y) is nitrogen, phosphorous, sulfur, or a combination thereof. For example, the positively charged member (Y) can be a nitrogen or phosphorous. In particular, the positively charged member (Y) is nitrogen, forming an amine with hydrocarbon groups (R1, R2, R3, or R4).

The positively charged member (Y) can be coupled to one or more hydrocarbon groups, such as at least two hydrocarbon groups, at least three hydrocarbon groups, or at least four hydrocarbon groups, but generally not greater than five hydrocarbon groups. As illustrated, the positively charged member (Y) includes four hydrocarbon groups (R1, R2, R3, or R4). The hydrocarbon groups (R1, R2, R3, or R4) independently can be an alkyl group, an aryl group, ether derivatives thereof, or combinations thereof. In an example, an alkyl hydrocarbon group can include a methyl, ethyl, propyl, or butyl group, an ether derivative thereof, or a combination thereof. For example, the propyl can be an n-propyl, an iso-propyl, or a combination thereof. In an example, the butyl group can be an n-butyl, isobutyl, sec-butyl, tert-butyl, or any combination thereof. An exemplary aryl group can include a phenyl, tolyl, xylyl, or poly-aryl, such as naphthyl, ether derivatives thereof, or any combination thereof.

In particular, the lipophilic counter ion [Y(R1)(R2)(R3)(R4)] can include a lipophilic ammonium ion, a lipophilic phosphonium ion, a lipophilic arsonium ion, a lipophilic sulfonium ion, or a combination thereof. An exemplary lipophilic ammonium ion includes a tetraalkylammonium, a tetraarylammonium, mixed alkyl and aryl ammonium, or a combination thereof. For example, an exemplary lipophilic ammonium ion is selected from the group consisting of tetramethylamonium, tetraethylamonium, tetrapropylamonium, tetrabutylamonium, tetrapentylamonium, tetrahexylamonium, tetraheptylamonium, tetraoctylamonium, alkyl and aryl mixtures thereof, and a combination thereof. An exemplary lipophilic phosphonium ion includes tetraphenylphosphonium. An exemplary lipophilic arsonium ion is a tetraalkylarsonium, a tetraarylarsonium, a mixed alkyl and aryl arsonium ion, or a combination thereof. For example, the lipophilic arsonium ion is tetraphenylarsonium. An exemplary lipophilic sulfonium ion is a trialkylsulfonium ion. The ion (Z) can be an ion of opposite charge to the lipophilic group [Y(R1)(R2)(R3)(R4)], such as a hydroxide, a halogen, a nitrate, a carbonate, a sulfate, a perchlorate, a phenolate, a tetraalkylborate, a tetraarylborate, a phosphate ion, or any combination thereof.

As a result of the exchange, the nucleic acid complex exhibits lipophilic behavior and can be dispersed in a nonaqueous solvent. In an example, the nonaqueous solvent is polar. In a further example, the nonaqueous solvent is not reactive with coupling groups on the substrate or functional groups of the polymer, such as the reactive group (W) of the nucleic acid complex. In an example, the solvent includes an amide, a urea, a carbonate, an ether, a sulfoxide, a sulfone, a hindered alcohol, or a combination thereof. An exemplary amide or urea includes formamide, N,N-dimethylformamide, acetamide, N,N-dimethylacetamide, hexamethylphosphoramide, pyrrolidone, N-methylpyrrolidone, N,N,N',N'-tetramethylurea, N,N'-dimethyl-N,N'-trimethyleneurea, or a combination thereof. An exemplary carbonate includes dimethyl carbonate, propylene carbonate, or a combination thereof. An exemplary ether includes tetrahydrofuran. An exemplary sulfoxide or sulfone includes dimethylsulfoxide, dimethylsulfone, or a combination thereof. An exemplary hindered alcohol includes tert-butyl alcohol.

Following the ion exchange or as part of the ion exchange, the nucleic acid complex can be dispersed in the nonaqueous solvent. The dispersed nucleic acid complex can be used for conjugation of a substrate.

Figure 7:
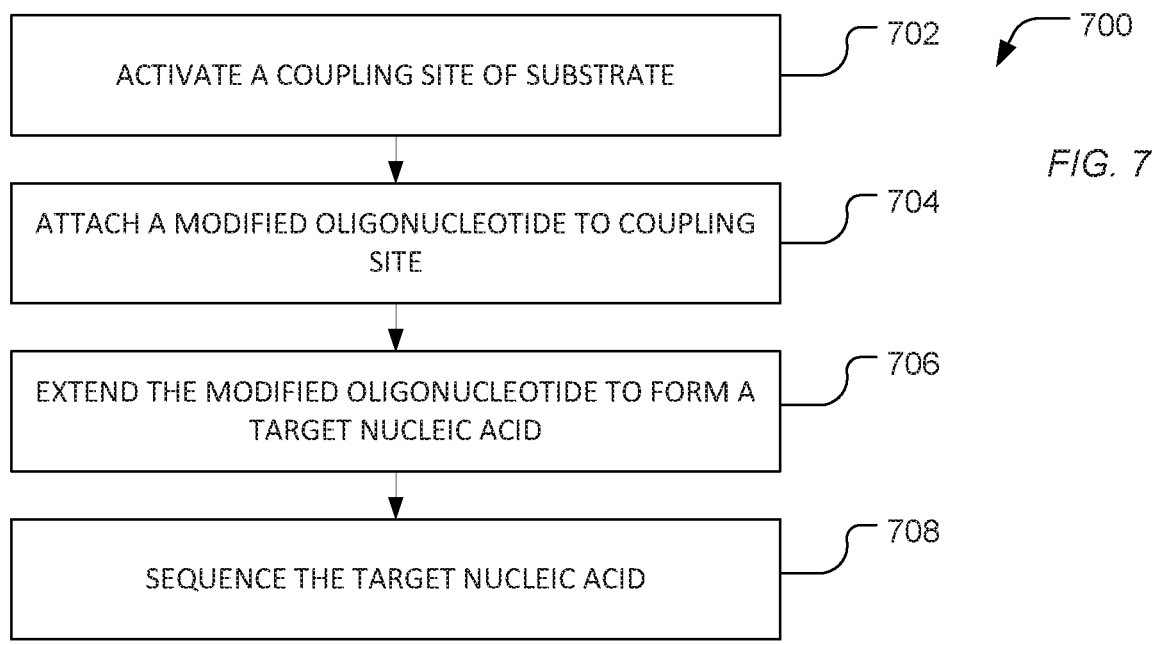
FIG. 7 includes a flow diagram illustrating an exemplary method for preparing and utilizing a substrate conjugated to an oligonucleotide.

To conjugate the ion exchanged oligonucleotide, coupling sites of a substrate can be activated to allow binding of linking moieties of the oligonucleotide to the coupling site. As illustrated in FIG. 7, a method 700 includes activating a coupling site of the substrate, as illustrated 702. Activating the coupling site depends on the nature of the coupling site. Exemplary coupling sites can include hydroxyl, amine, or carboxyl sites on a polymer network. Depending on the nature of coupling site of the substrate and activation chemistry, a linker moiety can be selected for the oligonucleotide.

Once activated, the modified oligonucleotide can be attached to the coupling site, as illustrated at 704. In particular, the modified nucleotide is coupled between the terminal end of the oligonucleotide and the coupling site. For example, the functional moiety can be attached to the oligonucleotide at the 5' end of the oligonucleotide, and the modified oligonucleotide can be coupled through a linker to the coupling site.

As illustrated at 706, the oligonucleotide can be extended to form a target nucleic acid. For example, a template including a segment complementary to the oligonucleotide can hybridize with the oligonucleotide, and the oligonucleotide can be extended to form a complement of the template nucleic acid. In particular, the resulting target nucleic acid is coupled to the coupling site of the substrate, and a dye moiety is coupled between the terminal end of the target nucleic acid and the coupling site of the substrate. In particular, the dye modified nucleic acid can be coupled between the 5' end of the target nucleic acid and the coupling site of the substrate.

As illustrated 708, the target nucleic acid conjugated to the substrate can be sequenced.

In a particular example, the substrate can include a polymer network. In an example, the polymer network includes a hydrogel network. The hydrogel network can for discrete separated and free floating units. In a particular example, the hydrogel is a polyacrylamide hydrogel with coupling sites in the form of hydroxyl groups, amine groups, or carboxyl groups, or a combination thereof. Depending on the nature of the coupling sites, the polymer network can be activated to conjugation with the dye-modified oligonucleotide.

The polymer can be activated to facilitate conjugation with a target analyte, such as a polynucleotide. For example, functional groups on the polymer network can be enhanced to permit binding with target analytes or analyte receptors. In a particular example, functional groups of the hydrophilic polymer can be modified with reagents capable of converting the hydrophilic polymer functional groups to reactive moieties that can undergo nucleophilic or electrophilic substitution. For example, hydroxyl groups can be activated by replacing at least a portion of the hydroxyl groups with a sulfonate group or chlorine. Exemplary sulfonate groups can be derived from tresyl, mesyl, tosyl, or fosyl chloride, or any combination thereof. Sulfonate can act to permit nucleophiles to replace the sulfonate. The sulfonate may further react with liberated chlorine to provide a chlorinated groups that can be used in a process to conjugate the particles. In another example, amine groups on the hydrophilic polymer can be activated.

For example, target analyte or analyte receptors can bind to the hydrophilic polymer through nucleophilic substitution with the sulfonate group. In particular example, target analyte receptors terminated with a nucleophile, such as an amine or a thiol, can undergo nucleophilic substitution to replace the sulfonate groups on the surface of the hydrophilic polymer. As a result of the activation, a conjugated polymer network can be formed.

In another example, the sulfonated networks can be further reacted with mono- or multi-functional mono- or multi-nucleophilic reagents that can form an attachment to the polymer network while maintaining nucleophilic activity for oligonucleotides comprising electrophilic groups, such as maleimide. In addition, the residual nucleophilic activity can be converted to electrophilic activity by attachment to reagents comprising multi-electrophilic groups, which are subsequently to attach to oligonucleotides comprising nucleophilic groups.

In another example, a monomer containing the functional group can be added during the polymerization. The monomer can include, for example, an acrylamide containing a carboxylic acid, ester, halogen or other amine reactive group. The ester group may be hydrolyzed before the reaction with an amine terminated oligonucleotide.

Other conjugation techniques include the use of monomers that comprise hydrophobic protecting groups on amines during polymer network synthesis. De-protection of the amine group makes available a nucleophilic group that can be further modified with amine reactive bi-functional bis-electrophilic reagents that yield a mono-functional electrophilic group subsequent to attachment to the polymer network. Such an electrophilic group can be reacted with oligonucleotides having a nucleophilic group, such as an amine or thiol, causing attachment of the oligonucleotide by reaction with the vacant electrophile.

If the hydrogel network is prepared from a combination of amino- and hydroxyl-acrylamides, de-protection of the hydrogel particle results in a combination of nucleophilic amino groups and neutral hydroxyl groups. The amino groups can be modified with di-functional bis-electrophilic moieties, such as a di-isocyanate or bis-NHS ester, resulting in a hydrophilic polymer network reactive to nucleophiles. An exemplary bis-NHS ester includes bis-succinimidyl C2-C12 alkyl esters, such as bis-succinimidyl suberate or bis-succinimidyl glutarate.

Other activation chemistries include incorporating multiple steps to convert a specified functional group to accommodate specific desired linkages. For example, the sulfonate modified hydroxyl group can be converted into a nucleophilic group through several methods. In an example, reaction of the sulfonate with azide anion yields an azide substituted hydrophilic polymer. The azide can be used directly to conjugate to an acetylene substituted biomolecule via "CLICK" chemistry that can be performed with or without copper catalysis. Optionally, the azide can be converted to amine by, for example, catalytic reduction with hydrogen or reduction with an organic phosphine. The resulting amine can then be converted to an electrophilic group with a variety of reagents, such as di-isocyanates, bis-NHS esters, cyanuric chloride, or a combination thereof. In an example, using di-isocyanates yields a urea linkage between the polymer and a linker that results in a residual isocyanate group that is capable of reacting with an amino substituted biomolecule to yield a urea linkage between the linker and the biomolecule. In another example, using bis-NHS esters yields an amide linkage between the polymer and the linker and a residual NHS ester group that is capable of reacting with an amino substituted biomolecule to yield an amide linkage between the linker and the biomolecule. In a further example, using cyanuric chloride yields an amino-triazine linkage between the polymer and the linker and two residual chloro-triazine groups one of which is capable of reacting with an amino substituted biomolecule to yield an amino-triazine linkage between the linker and the biomolecule. Other nucleophilic groups can be incorporated into the polymer network via sulfonate activation. For example, reaction of sulfonated particles with thiobenzoic acid anion and hydrolysis of the consequent thiobenzoate incorporates a thiol into the polymer network which can be subsequently reacted with a maleimide substituted biomolecule to yield a thio-succinimide linkage to the biomolecule. Thiol can also be reacted with a bromo-acetyl group.

Alternatively, acrydite oligonucleotides can be used during the polymerization to incorporate oligonucleotides. An exemplary acrydite oligonucleotide can include an ion-exchanged oligonucleotides.

In an example in which the polymer network include carboxyl coupling sites, a carboxyl activating compound, such as a succinimidyl compound, can be applied to the polymer substrate, for example in a non-aqueous solvent. The succinimidyl compound can react with the carboxyl functionality, such as an alkanoic acid moiety or ester derivative thereof, to form a succinimidyl alkanoate moiety, referred to herein as activation. A succinimidyl compound can be applied to the polymer substrate. The succinimidyl compound, for example, can be a succinimidyl uronium compound or a succinimidyl phosphonium compound. In a particular example, the succinimidyl compound is a succinimidyl uronium compound. The succinimidyl uronium compound can be an O-type succinimidyl uronium. In an example, the O-type succinimidyl uronium is an N-hydroxy succinimidyl uronium. In another example, the succinimidyl compound is a succinimidyl phosphonium compound. For example, an N-hydroxy succinimidyl compound (NHS-compound) can react with the carboxyl functionality on the substrate, for example, in a non-aqueous solvent, to form the succinimidyl alkanoate compound (C(O)NHS). The modified polymer substrate can be conjugated to a biomolecule, such as a dye modified oligonucleotide or nucleic acid, by applying an amine-terminated biomolecule, for example, dissolved in a non-aqueous solvent, to the polymer substrate.

Covalent linkages of biomolecules onto refractory or polymeric substrates can be created using electrophilic moieties on the substrate coupled with nucleophilic moieties on the biomolecule or nucleophilic linkages on the substrate coupled with electrophilic linkages on the biomolecule. Because of the hydrophilic nature of most common biomolecules of interest, the solvent of choice for these couplings is water or water containing some water soluble organic solvent in order to disperse the biomolecule onto the substrate. In particular, polynucleotides are generally coupled to substrates in water systems because of their poly-anionic nature. Because water competes with the nucleophile for the electrophile by hydrolyzing the electrophile to an inactive moiety for conjugation, aqueous systems generally result in low yields of coupled product, where the yield is based on the electrophilic portion of the couple. When high yields of electrophilic portion of the reaction couple are desired, high concentrations of the nucleophile are required to drive the reaction and mitigate hydrolysis, resulting in inefficient use of the nucleophile. In the case of polynucleic acids, the metal counter ion of the phosphate can be replaced with a lipophilic counter-ion, in order to help solubilize the biomolecule in polar, non-reactive, non-aqueous solvents, as described above in relation to FIG. 6. These solvents can include amides or ureas such as formamide, N,N-dimethylformamide, acetamide, N,N-dimethylacetamide, hexamethylphosphoramide, pyrrolidone, N-methylpyrrolidone, N,N,N',N'-tetramethylurea, N,N'-dimethyl-N,N'-trimethyleneurea, or a combination thereof; carbonates such as dimethyl carbonate, propylene carbonate, or a combination thereof; ethers such as tetrahydrofuran; sulfoxides and sulfones such as dimethylsulfoxide, dimethylsulfone, or a combination thereof; hindered alcohols such as tert-butyl alcohol; or a combination thereof. Lipophilic cations can include tetraalkylammomiun or tetraarylammonium cations such as tetramethylamonium, tetraethylamonium, tetrapropylamonium, tetrabutylamonium, tetrapentylamonium, tetrahexylamonium, tetraheptylamonium, tetraoctylamonium, and alkyl and aryl mixtures thereof, tetraarylphosphonium cations such as tetraphenylphosphonium, tetraalkylarsonium or tetraarylarsonium such as tetraphenylarsonium, and tri-alkylsulfonium cations such as trimethylsulfonium, or a combination thereof. The conversion of polynucleic acids into organic solvent soluble materials by exchanging metal cations with lipophilic cations can be performed by a variety of standard cation exchange techniques.

Figure 8:
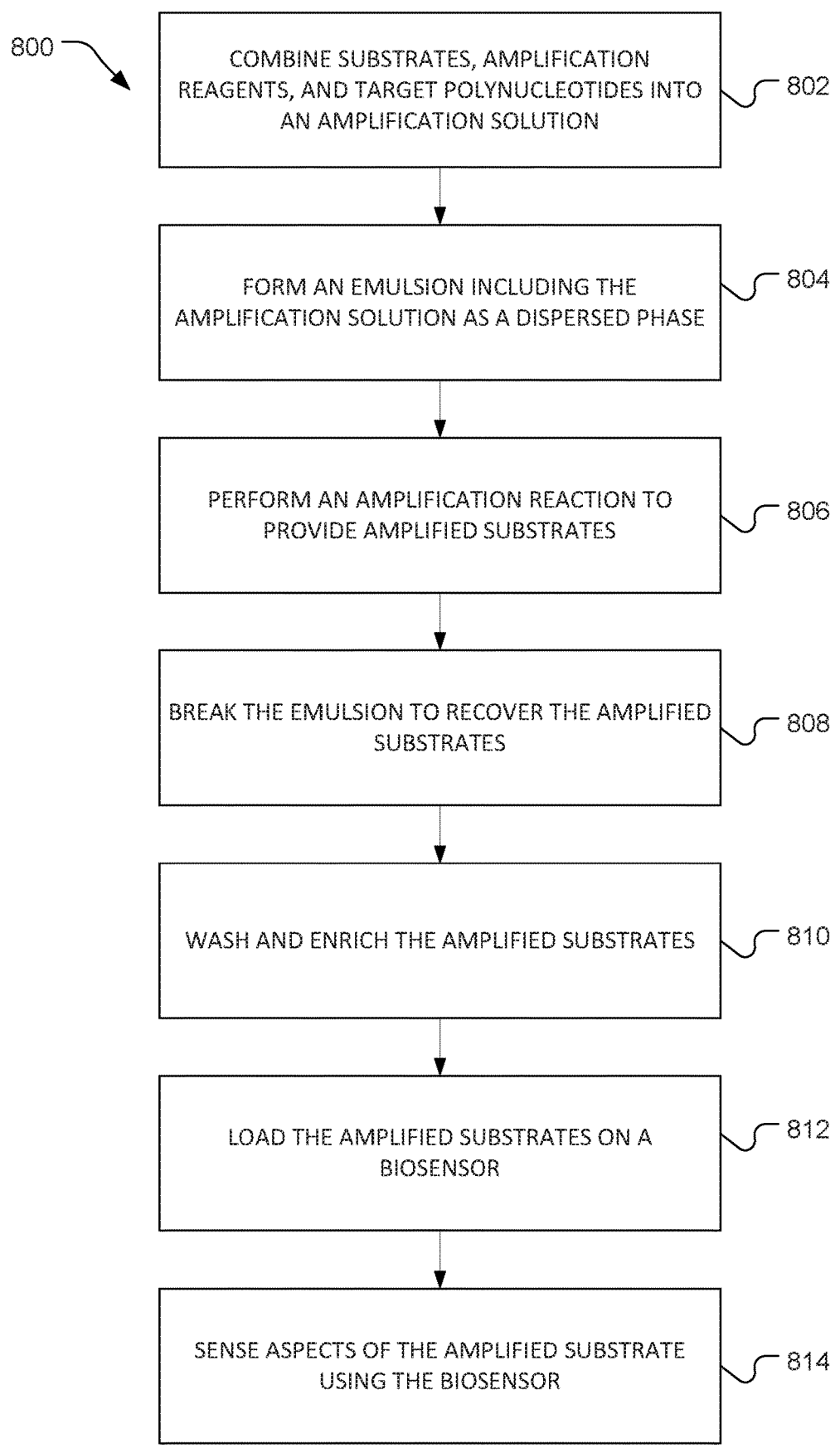
FIG. 8 includes a flow diagram illustrating an exemplary method for preparing and using substrates conjugated to nucleic acids.

In a particular example, the substrates are conjugated with nucleic acids prior to depositing the substrates on a sensor substrate including wells. As illustrated in FIG. 8, a method 800 includes combining substrates, amplification reagents, and target polynucleotides into an amplification solution, as illustrated at 802. In particular, substrates can be formed of hydrophilic polymers. In an example, the substrates can carry a charge. Alternatively, the substrates can be neutral. The substrates are conjugated to a modified oligonucleotide, such as a dye modified oligonucleotide, a buffer modified oligonucleotide, or a combination thereof.

For example, the substrates can be formed from monomers including a radically polymerizable monomer, such as a vinyl-based monomer. In an example, the monomer can include acrylamide, vinyl acetate, hydroxyalkylmethacrylate, or any combination thereof. In a particular example, the hydrophilic monomer is an acrylamide, such as an acrylamide including hydroxyl groups, amino groups, carboxyl groups, or a combination thereof. In an example, the hydrophilic monomer is an aminoalkyl acrylamide, an acrylamide functionalized with an amine terminated polypropylene glycol, an acrylopiperazine, or a combination thereof. In another example, the acrylamide can be a hydroxyalkyl acrylamide, such as hydroxyethyl acrylamide. In particular, the hydroxyalkyl acrylamide can include N-tris(hydroxymethyl)methyl)acrylamide, N-(hydroxymethyl)acrylamide, or a combination thereof. In a further example, a mixture of monomers, such as a mixture of hydroxyalkyl acrylamide and amine functionalize acrylamide or a mixture of acrylamide and amine functionalized acrylamide, can be used. In an example, the amine functionalize acrylamide can be included in a ratio of hydroxyalkyl acrylamide:amine functionalized acrylamide or acrylamide:amine functionalized acrylamide in a range of 100:1 to 1:1, such as a range of 100:1 to 2:1, a range of 50:1 to 3:1, a range of 50:1 to 5:1 or even a range of 50:1 to 10:1.

In another example, the monomer can include a carboxyl coupling site and, for example, can have the formula:

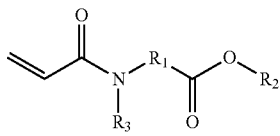

wherein $R_1$ is an alkyl group having between 3 and 10 carbons, is a polyether group having between 1 and 10 ether units, or is another non-ionic polar group, wherein $R_2$ is hydrogen, a linear or branched alkyl group having between 3 and 8 carbons or is a silyl group, and wherein $R_3$ is hydrogen or an alkyl group having between 1 and 6 carbons. In a particular example, $R_1$ is an alkyl group having between 3 and 10 carbons or is a polyether group having between 1 and 10 ether units. For example, $R_1$ can be an alkyl group having 3 to 6 carbons, such as 3 to 5 carbons. In another example, $R_1$ can be a polyether group including units, such as including ethylene oxide or propylene oxide units, in a range of 2 to 6 units, such as 2 to 4 units. In a further example, R1 can be a non-ionic polar group, for example, including an amide. In an example, $R_2$ is a branched alkyl group, for example, having 3 to 5 carbons, such as 4 carbons. In particular, $R_2$ can be an isopropyl, isobutyl, sec-butyl, or tert-butyl group, or any combination thereof. The silyl group can be a trialkyl silyl group, an organo disilyl group, or an organo trisilyl group. For example, the trialkyl silyl group can be a trimethyl silyl or a triethyl silyl group. In a particular example, $R_2$ is hydrogen. In a further example, $R_3$ is hydrogen. In another example, $R_3$ is a methyl or ethyl group.

In a particular example, the substrates are hydrogel beads.

Each of the substrates can include coupling sites attached to oligonucleotide primers to which a template polynucleotide can hybridize. For example, the coupling sites can each be attached to a coupling oligonucleotide complementary to a section of a template polynucleotide. The template polynucleotide can include the target polynucleotide or segments complementary to the target polynucleotide, in addition to segments complementary to the coupling oligonucleotide.

The coupling oligonucleotide can be conjugated to the substrates. The polymer of a substrate can be activated to facilitate conjugation with a target analyte, such as an oligonucleotide or polynucleotide. For example, functional groups on the substrates can be enhanced to permit binding with target analytes or analyte receptors.

The substrates can be incorporated into the amplification solution along with amplification reagents, such as enzymes including polymerase or recombinase, nucleotides (e.g. A, T, C, G, or analogs thereof), various salts or ionic compounds, or a combination thereof. In particular, target polynucleotides, such as polynucleotides derived from biological sources, are included in the amplification solution.

An emulsion is formed that includes the amplification solution as a dispersed phase, as illustrated in 804. In particular, the amplification solution is an aqueous solution and can be dispersed in a hydrophobic phase, such as an oil phase. The hydrophobic phase can include fluorinated liquids, minerals oils, silicone oils, or any combination thereof. Optionally, the hydrophobic phase can include a surfactant, such as a non-ionic surfactant, such as the non-ionic surfactant described below.

The emulsion can be formed utilizing a membrane-based mechanism, in which the aqueous amplification solution and the continuous phase hydrophobic liquid are passed through a membrane one or more times, forming droplets of the amplification solution within the continuous phase hydrophobic liquid. Alternatively, the emulsion can be formed by agitating the amplification solution in the presence of the hydrophobic liquid. In another example, the emulsion can be formed by repeatedly aspirating and ejecting the amplification solution and the hydrophobic continuous phase through a pipette tip. In a further example, droplets of the aqueous amplification solution can be injected into a stream of the hydrophobic liquid.

Following the emulsification of the amplification solution, droplets of amplification solution forming a dispersed phase can include substrates and a target polynucleotide. A portion of the droplets can include one or more substrates and a single target polynucleotide. Other droplets can include substrates and no polynucleotide. Other droplets can include one or more substrates and more than one target polynucleotides.

Figure 9:
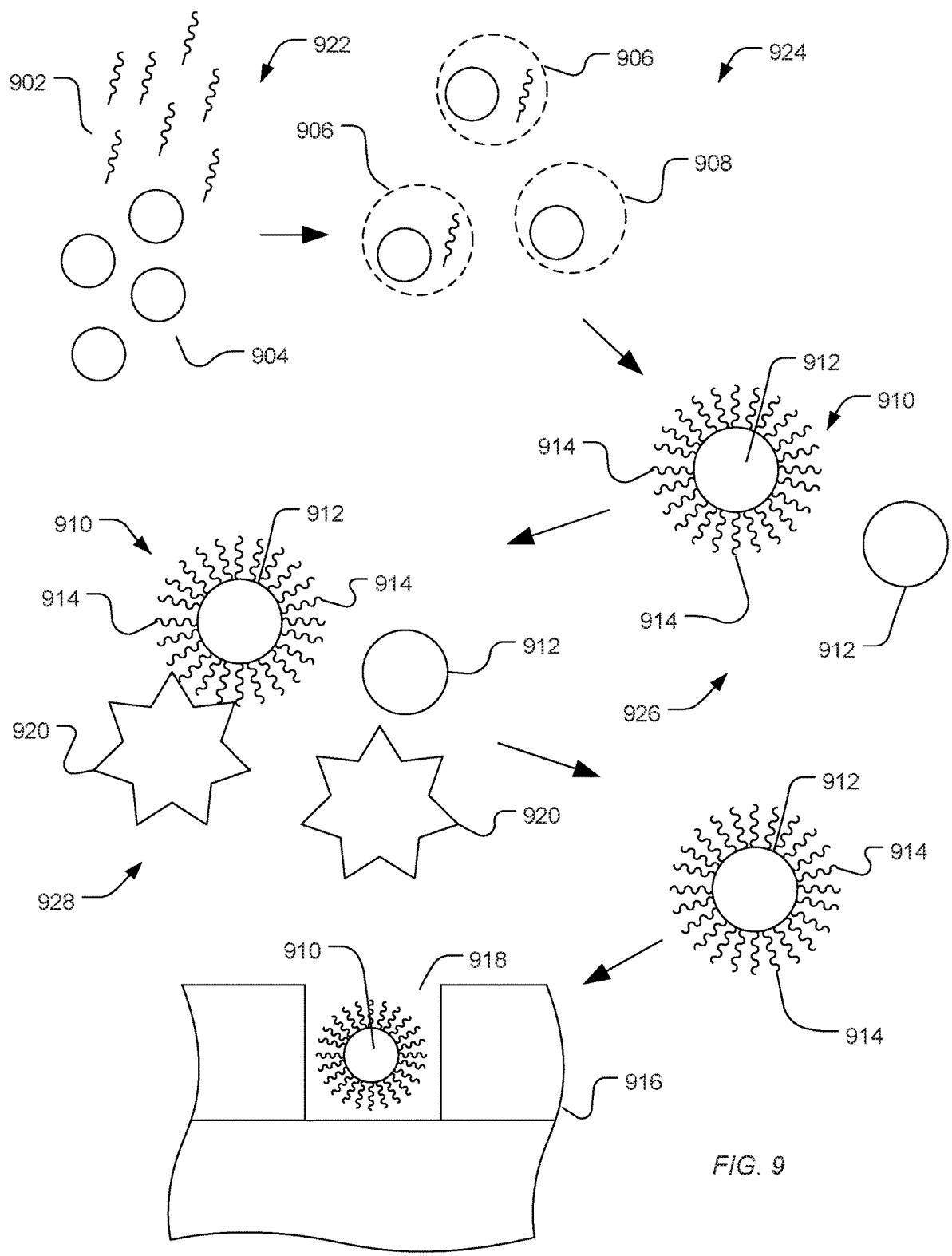
FIG. 9 includes an illustration of an exemplary emulsion-based method for preparing discrete substrates for use in a sequencing device.

For example, as illustrated in FIG. 9, an aqueous amplification solution 922 includes target polynucleotides 902 and substrates 904. Following emulsification, some droplets 906 of the emulsion 924 can include a single target polynucleotide and one or more substrates. Other droplets 908 of the emulsion 924 can include a substrate and no target polynucleotide. The substrates can include conjugated modified oligonucleotide, which, for example, is complementary to a portion of the target polynucleotide.

Returning to FIG. 8, an amplification reaction can be performed to provide nucleic acid substrates, as illustrated at 806. The nucleic acid substrates include the substrate and conjugated copies of nucleic acids. The conditions of the amplification reaction can depend on factors, such as the nature of the enzymes used in the amplification solution, the concentration of individual nucleotides, a concentration of salts or ionic compounds, among other factors. In an example, the amplification reaction is a polymerase chain reaction (PCR) in which the temperature cycles multiple times in a range of 40° C. to 100° C. In another example, the amplification reaction is a recombinase polymerase amplification (RPA). Such reactions can be performed isothermally at a temperature in a range of 40° C. to 90° C. Other amplification techniques can be used, for example, polymerase cycling assembly (PCA), asymmetric PCR, helicase-dependent amplification, ligation-mediated PCR, multiplex-PCR, nanoparticle-assisted PCR, or other amplification techniques. Optionally, amplification can be performed without an emulsion.

In an example, during amplification, template polynucleotides including a target sequence of interest and a segment complementary to the coupling oligonucleotide hybridize to the coupling oligonucleotide. The coupling oligonucleotide is extended, forming a complement to the template polynucleotide. The template polynucleotide can further include a capture moiety useful for binding with a separation substrate for later separation of amplified substrates from unamplified substrates.

As a result of the amplification, dispersed phase droplets including target polynucleotides and substrates produce nucleic acid substrates including one or more copies of the target polynucleotide conjugated to the substrates. In contrast, droplets including a substrate and lacking a target polynucleotide do not produce substrates that include copies of target polynucleotides and are referred to herein as unamplified substrates.

As illustrated at 808, the emulsion is broken to recover nucleic acid substrates, whereby the liquid of the dispersed phase is separated from the continuous phase. For example, the emulsion can be applied over a breaking solution and optionally agitated or centrifuged. In particular, centrifuging the emulsion through a breaking solution drives substrates into the breaking solution away from an interface between the breaking solution and the continuous phase liquid of the emulsion. The breaking solution can be a hydrophilic liquid, such as an aqueous solution that includes surfactants to assist with augmenting surface tensions and separating the dispersed phase from the continuous phase.

In an example, the breaking solution can include one or more surfactants having a total concentration in the range of 0.01% to 20% by weight. For example, the surfactant can be included in an amount in a range of 0.1% to 15.0%, such as a range of 0.5% to 10.0%, a range of 0.5% to 5.0% or even a range of 0.5% to 3% by weight. In another example, the surfactant can be included in a total amount in a range of 5.0% to 20.0%, such as a range of 10.0% to 20.0%, or a range of 12.0% to 18.0%.

The surfactant can be an ionic surfactant, an amphoteric surfactant, a non-ionic surfactant, or a combination thereof. The ionic surfactant can be an anionic surfactant. An exemplary anionic surfactant includes a sulfate surfactant, a sulfonate surfactant, a phosphate surfactant, a carboxylate surfactant, or any combination thereof. An exemplary sulfate surfactant includes alkyl sulfates, such as ammonium lauryl sulfate, sodium lauryl sulfate (sodium dodecyl sulfate, (SDS)), or a combination thereof; an alkyl ether sulfate, such as sodium laureth sulfate, sodium myreth sulfate, or any combination thereof; or any combination thereof. An exemplary sulfonate surfactant includes an alkyl sulfonate, such as sodium dodecyl sulfonate; docusates such as dioctyl sodium sulfosuccinate; alkyl benzyl sulfonate (e.g., dodecyl benzene sulfonic acid or salts thereof); or any combination thereof. An exemplary phosphate surfactant includes alkyl aryl ether phosphate, alkyl ether phosphate, or any combination thereof. An exemplary carboxylic acid surfactant includes alkyl carboxylates, such as fatty acid salts or sodium stearate; sodium lauroyl sarcosinate; a bile acid salt, such as sodium deoxycholate; or any combination thereof.

In another example, the ionic surfactant can be a cationic surfactant. An exemplary cationic surfactant includes primary, secondary or tertiary amines, quaternary ammonium surfactants, or any combination thereof. An exemplary quaternary ammonium surfactant includes alkyltrimethylammonium salts such as cetyl trimethylammonium bromide (CTAB) or cetyl trimethylammonium chloride (CTAC); cetylpyridinium chloride (CPC); polyethoxylated tallow amine (POEA); benzalkonium chloride (BAC); benzethonium chloride (BZT); 5-bromo-5-nitro-1,3-dioxane; dimethyldioctadecylammonium chloride; dioctadecyldimethylammonium bromide (DODAB); or any combination thereof.

An exemplary amphoteric surfactant includes a primary, secondary, or tertiary amine or a quaternary ammonium cation with a sulfonate, carboxylate, or phosphate anion. An exemplary sulfonate amphoteric surfactant includes (3-[(3-cholamidopropyl) dimethylammonio]-1-propanesulfonate); a sultaine such as cocamidopropyl hydroxysultaine; or any combination thereof. An exemplary carboxylic acid amphoteric surfactant includes amino acids, imino acids, betaines such as cocamidopropyl betaine, or any combination thereof. An exemplary phosphate amphoteric surfactant includes lecithin.

In another example, the surfactant can be a non-ionic surfactant such as a polyethylene glycol-based surfactant, an alkyl pyrrolidine surfactant, an alkyl imidazolidinone surfactant, an alkyl morpholine surfactant, an alkyl imidazole surfactant, an alkyl imidazoline surfactant, or a combination thereof. In a particular example, the polyethylene-glycol-based surfactant includes a polyethylene-glycol ether, such as an alkylphenol polyethoxylate. In another example, the non-ionic surfactant includes a non-ionic fluorosurfactant, such as an ethoxylated fluorocarbon. In a further example, the surfactant solution can include octyl pyrrolidine.

In particular, the surfactant solution can include combinations of such surfactants. For example, the surfactant solution can include a combination of a non-ionic surfactant with an anionic surfactant. In a particular example, the surfactant solution can include a non-ionic surfactant, such as a polyethylene glycol ether, an alkyl pyrrolidine, or a non-ionic fluorosurfactant, and an anionic surfactant, such as a sulfate surfactant, for example SDS. In particular, the surfactant solution can include an ionic surfactant, such as an anionic surfactant, in an amount in a range of 0.1% to 20.0%, such as a range of 1.0% to 15.0%, or a range of 5.0% to 15.0%, or a range of 8.0% to 12.0%. In addition, the surfactant solution can include a non-ionic surfactant, such as alkyl pyrrolidine (e.g., octyl pyrrolidine) in a range of 0.01% to 10.0%, such as a range of 0.05% to 8.0%, or a range of 1.0% to 6.0%. In another example, the surfactant solution can include a non-ionic surfactant in a range of 0.05% to 3.0%.

Referring to FIG. 9, following emulsion breaking, the remaining aqueous solution 926 includes nucleic acid substrates 910. The nucleic acid substrates 910 can include the substrates 912 conjugated to a plurality of copies of the target polynucleotide 914. The solution can also include substrates 912 that do not include copies of target polynucleotides, referred to herein as unamplified substrates.

Returning to FIG. 8, the nucleic acid substrates are washed and enriched, as illustrated at 810. In an example, the substrates can be pelletized using centrifugation and excess solution can be decanted or drawn from above the pelletized substrates. In another example, the nucleic acid substrates can be attached to separation substrates used to secure the nucleic acid substrates while the aqueous solution surrounding the nucleic acid substrates is replaced.

For example, as illustrated in FIG. 9, nucleic acid substrates 910 can be captured by a separation substrate 920. In contrast, the unamplified substrates 912 that do not include copies of polynucleotides do not readily attached to the separation substrate 920. Thus, when the separation substrate 920 is secured and the attached nucleic acid substrates 910 are held in place, the unsecured unamplified substrates are substantially washed from the solution. In a particular example, the separation substrates 914 are magnetic substrates that can be secured to a container wall using a magnetic field. The nucleic acid substrates 210 can then be separated from the separation substrates 920 providing a solution that has predominantly nucleic acid substrates and substantially fewer unamplified substrates.

In a particular example, the nucleic acid substrates 910 can include a capture moiety that interacts with moieties on the separation substrates 920. The unamplified substrates can be substantially free of the capture moieties. For example, the template polynucleotide can be terminated with a capture moiety. The unamplified substrates not hybridized to a template polynucleotide lack the capture moiety and thus, do not bind with the separation substrate. Once the nucleic acid substrates 910 are separated from the unamplified substrates, the nucleic acid substrates 910 can be separated from the separation substrate, for example, by melting or detaching the template polynucleotide from the extended coupling oligonucleotides conjugated to the nucleic acid substrates 910.

Returning to FIG. 8, the enriched nucleic acid substrates can be loaded onto a biosensor, as illustrated at 812. Depending upon the nature of the biosensor, the biosensor can provide a surface onto which the nucleic acid substrates can be attached. The surface can be flat and optionally can include regions that are more attractive to the nucleic acid substrates or that are modified to secure the nucleic acid substrates. In another example, the biosensor can include a surface that includes discrete sites or patterned surfaces, such as dimples, depressions, pores, wells, ridges or channels into which the nucleic acid beads align. In a further example, as illustrated in FIG. 9, the biosensor can include a surface structure 916 that defines a well 918 into which the nucleic acid substrates 910 are deposited.

In a particular example, the well is defined over a sensor. The well walls or the sensor can have surfaces formed of metals, semi-metals, oxides thereof, nitrides thereof, or a combination thereof. In an example, the well wall can be formed of a semi-metal, such as silicon, an oxide thereof such as silicon dioxide, a nitride thereof such as silicon nitride, or a combination thereof. In another example, the wall of the well can be formed at least partially of a metal or metal oxide. Exemplary metals include titanium, tungsten, tantalum, hafnium, aluminum, zirconium, zinc, or a combination thereof. A portion of the well wall can be formed of an oxide or nitride of such metals, such as, for example, titanium oxide, tantalum oxide, hafnium oxide, aluminum oxide, zirconium oxide, titanium nitride, among others, or a combination thereof. Further, the sensor forming a bottom of the well can have a metal, metal oxide, or metal nitride surface, or a combination thereof. Exemplary metals include titanium, tungsten, tantalum, hafnium, aluminum, zirconium, or zinc, or a combination thereof. Exemplary metal oxides or nitrides include titanium oxide, tantalum oxide, hafnium oxide, aluminum oxide, zirconium oxide, titanium nitride, among others, or a combination thereof.

In a particular example, the walls of the well or a surface of the sensor can have hydroxyl groups, for example, in a concentration in a range of 8 to 20 OH/nm$^2$, such as between 8 and 16 OH/nm$^2$. Optionally, the surface can be treated with a sulfate, phosphate, or silane containing compound. The compound can bind to at least a portion of the OH groups residing on the surface of the well wall or sensor. In a particular example, the compound includes a silane containing compound, such as butyl ammonium trimethoxy silane (BATS) or a phosphonic acid containing compound, such as an imidazole alkyl phosphonic acid, e.g., (1-methyl-3-(dodecylphosphonic acid) imidazolium bromide) (ImPA).

As illustrated at 814 of FIG. 8, the biosensor can sense aspects of the nucleic acid substrates. Depending upon the nature of the biosensor, the sensor can be utilized to detect the presence of particular sequences within the target polynucleotide, or can be used to sequence the target polynucleotide. For example, the biosensor can utilize fluorescence-based sequencing-by-synthesis. In another example, the biosensor can utilize techniques for sequencing that include sensing byproducts of nucleotide incorporation, such as pH or the presence of pyrophosphate or phosphate. In a further example, the biosensor can utilize temperature or heat detection.

Returning to FIG. 9, in an example, a well 918 of an array of wells can be operatively connected to measuring devices. For example, for fluorescent emission methods, a well 918 can be operatively coupled to a light detection device. In the case of ionic detection, the lower surface of the well 918 can be disposed over a sensor pad of an ionic sensor, such as a field effect transistor.

One exemplary system involving sequencing via detection of ionic byproducts of nucleotide incorporation includes semiconductor sequencing platforms, such as an ion-based sequencing system that sequences nucleic acid templates by detecting hydrogen ions produced as a byproduct of nucleotide incorporation. Typically, hydrogen ions are released as byproducts of nucleotide incorporations occurring during template-dependent nucleic acid synthesis by a polymerase. Such a sequencer detects the nucleotide incorporations by detecting the hydrogen ion byproducts of the nucleotide incorporations. Such a sequencer can include a plurality of template polynucleotides to be sequenced, each template disposed within a respective sequencing reaction well in an array. The wells of the array can each be coupled to at least one ion sensor that can detect the release of H+ ions or changes in solution pH produced as a byproduct of nucleotide incorporation. The ion sensor comprises a field effect transistor (FET) coupled to an ion-sensitive detection layer that can sense the presence of H+ ions or changes in solution pH. The ion sensor can provide output signals indicative of nucleotide incorporation which can be represented as voltage changes whose magnitude correlates with the H+ ion concentration in a respective well or reaction chamber. Different nucleotide types can be flowed serially into the reaction chamber, and can be incorporated by the polymerase into an extending primer (or polymerization site) in an order determined by the sequence of the template. Each nucleotide incorporation can be accompanied by the release of H+ ions in the reaction well, along with a concomitant change in the localized pH. The release of H+ ions can be registered by the FET of the sensor, which produces signals indicating the occurrence of the nucleotide incorporation. Nucleotides that are not incorporated during a particular nucleotide flow may not produce signals. The amplitude of the signals from the FET can also be correlated with the number of nucleotides of a particular type incorporated into the extending nucleic acid molecule thereby permitting homopolymer regions to be resolved. Thus, during a run of the sequencer multiple nucleotide flows into the reaction chamber along with incorporation monitoring across a multiplicity of wells or reaction chambers can permit the instrument to resolve the sequence of many nucleic acid templates simultaneously.

Figure 10:
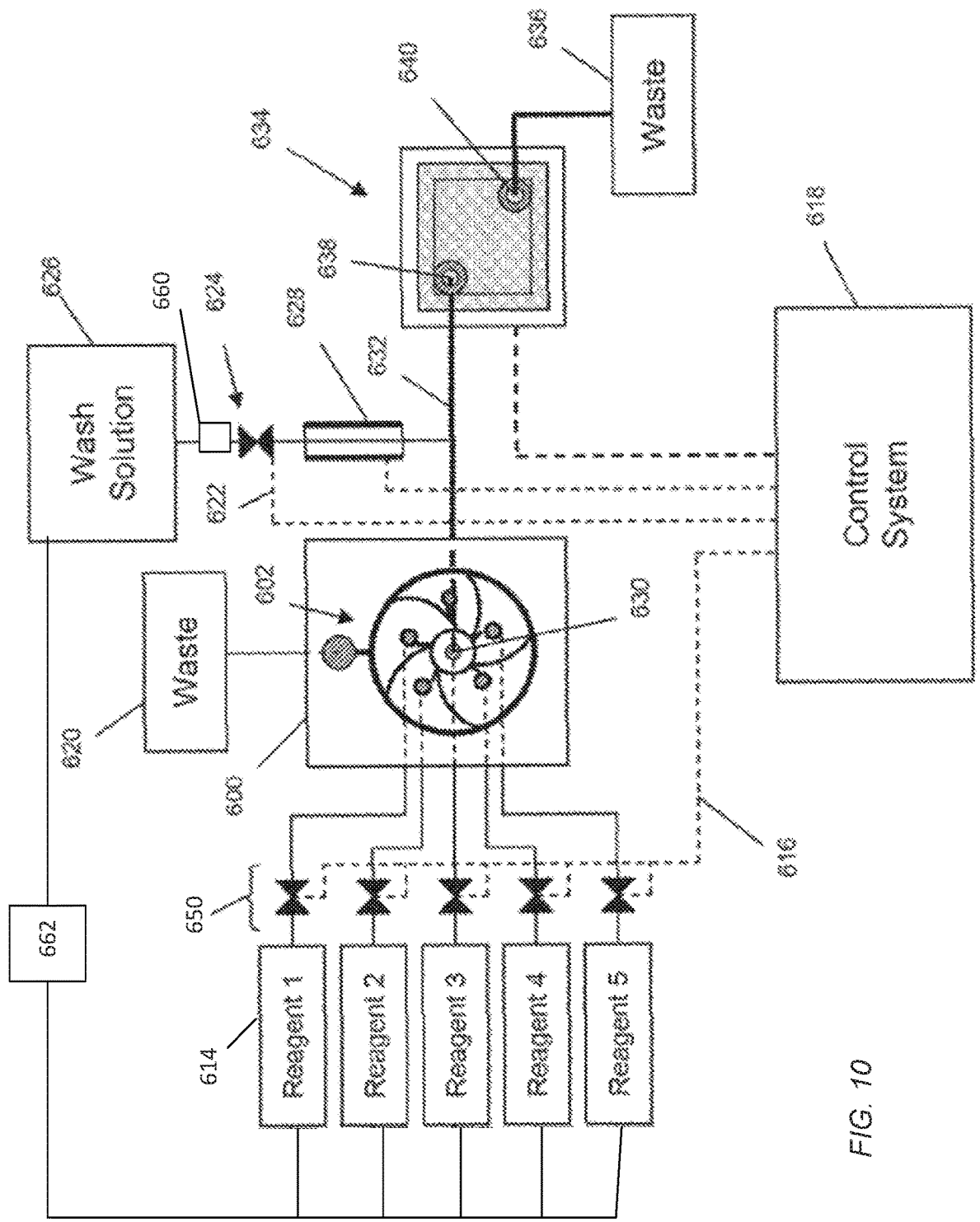
FIG. 10 includes an illustration of an exemplary sequencing system.

FIG. 10 includes an illustration of a more detailed embodiment of the fluidic circuit. FIG. 10 diagrammatically illustrates a system employing an enclosure 614 that is a reagent reservoir, for example, for carrying out pH-based nucleic acid sequencing. Each electronic sensor of the apparatus generates an output signal. The fluid circuit permits multiple reagents to be delivered to the reaction chambers.

In FIG. 10, the system includes a fluidics circuit 602 connected to the reagent reservoirs 614, to a waste reservoir 620, and to a biosensor 634 by fluid pathway 632 that connects fluidics node 630 to inlet 638 of biosensor 634 for fluidic communication. The prepared and mixed reagent solution from reservoirs 614 can be driven to fluidic circuit 602 by a variety of methods including pressure, pumps, such as syringe pumps, gravity feed, and the like, and are selected by control of valves 650. Reagents from the fluidics circuit 602 can be driven to the waste containers 620 and 636. The control system 618 includes controllers for valves 650 that generate signals for opening and closing via an electrical connection 616.

The control system 618 also includes controllers for other components of the system, such as a wash solution valve 624 connected thereto by the electrical connection 622, and the reference electrode 628. The control system 618 can also include control and data acquisition functions for the biosensor 634. In one mode of operation, the fluidic circuit 602 delivers a sequence of selected reagents 1, 2, 3, 4, or 5 to the biosensor 634 under programmed control of the control system 618, such that in between selected reagent flows, the fluidics circuit 602 is primed and washed with a wash solution 626, and the biosensor 634 is washed with the wash solution 626. Fluids entering the biosensor 634 exit through the outlet 640 and are deposited in the waste container 636. A similar setup may be used for optical sequencing systems, with photodiodes or CCD cameras, for example.

In a particular example, the wash solution 626 can be a buffered suspension including the solid buffer particulate. The buffer suspension (wash solution) can be filtered using a filter 660 before entering the fluidics circuit 602 or sensor 634. In a further example, the buffered suspension can be applied to the reagent reservoirs 614 through filter 662 to form the reagent solutions from reagent concentrate within the reagent reservoirs. Alternatively, the filter 660 and 662 can be the same filter. In an example, the reagent concentrate is a liquid concentrate. In another example, the reagent concentrate is a dried concentrate, such as a lyophilized reagent (e.g., lyophilized nucleotides). Alternatively, the illustrated filters 660 and 662 can be combined. In another example, filters can be located downstream of the reagent reservoirs 614, such as between the reagent reservoirs 614 and the valves 650.

Examples

Utilizing Proton™ sequencing kits with sequencing performed on an ION Torrent™ Proton sequencer, polyacrylamide particles conjugated to modified oligonucleotides are tested for functionality and sequencing performance. Standard protocols for the kits are followed, with the exception of the type of beads utilized.

ION Spheres of the Proton sequencing kits are replaces with polyacrylamide beads conjugated to TAMRA modifier oligonucleotides and FAM modified nucleotides. The beads undergo PCR with sample target nucleotides, loaded on Proton chips and sequenced. Both types of beads exhibit greater than 93% loading and greater than 98% raw read accuracy.

Polyacrylamide beads are formed with a polyethylene glycol space between the dye labeled nucleotide and the remainder of the oligonucleotide. Such beads are sequenced for comparison with beads not having the PEG spacer. Beads having the spacer exhibit similar size and label density to beads not having spacers. But, beads without spacers exhibit more than 30% greater AQ20 mean.

Oligonucleotides modified with functional moieties can be used in sequencing reactions with limited impact on enzyme activity and overall sequencing performance.

In a first aspect, a method of forming a nucleic acid substrate includes activating a coupling site of a substrate and binding a linker moiety coupled to a terminal end of an oligonucleotide to the activated coupling site. A functional moiety is coupled between the terminal end of the oligonucleotide and the linker moiety.

In a second aspect, a method of forming a nucleic acid substrate includes exposing a substrate conjugated to an oligonucleotide at a coupling site to an enzyme, nucleotides, and a target polynucleotide complementary to at least a portion of the oligonucleotide under conditions to facilitate extension of the oligonucleotide. A functional moiety is bound between the oligonucleotide and the coupling site. The method also includes washing the substrate following extension of the oligonucleotide.

In a third aspect, a method of sequencing a nucleic acid target includes applying a discrete substrate to a sequencing device. The discrete substrate is conjugated to a terminal end of the nucleic acid target at a coupling site of the discrete substrate. A functional moiety is coupled between the terminal end of the nucleic acid and the substrate. The method further includes applying a primer complementary to a portion of the target nucleic acid, flowing a nucleotide into the sequencing device, and detecting an incorporation event associated with the nucleotide.

In a fourth aspect, a hydrogel network includes a hydrogel polymer having a coupling site, an oligonucleotide conjugated at a terminal end to the hydrogel polymer at the coupling site, and a functional moiety coupled between the terminal end of the oligonucleotide and the coupling site.

In an example of the above aspects, the terminal end is the 5' end of the oligonucleotide.

In another example of the above aspects and examples, the methods further include performing ion exchange on the oligonucleotide.

In a further example of the above aspects and examples, the functional moiety is a dye moiety. For example, the dye moiety is a rhodamine moiety. In another example, the dye moiety is a fluorescein moiety.

In an additional example of the above aspects and examples, the functional moiety is a buffer moiety. In an example, the buffer moiety is morpholinoalkyl, triethanolamine, N-[tris(hydroxymethyl) methyl]-2-aminoethanesulfonic acid, 3-(N-tris[hydroxymethyl]methylamino)-2-hydroxypropanesulfonic acid, N-(2-hydroxyethyl)piperazine-N-(2-ethanesulfonic acid), N-(2-acetamido)-2-aminoethanesulfonic acid, imidazole, acetate, or any combination thereof.

In another example of the above aspects and examples, the functional moiety is attached to a modified nucleotide. For example, the modified nucleotide includes a pyrmidine base, the functional moiety coupled to the pyrimidine base. In an example, the functional moiety is attached to the 5-position of the pyrimidine base. In a particular example, the pyrimidine base includes thymidine or cytidine. In another example, the modified nucleotide includes a 7-deaza-purine base. In an example, the functional moiety is attached to the 7-position of the 7-deaza-purine base. In a particular example, the 7-deaza-purine base include guanosine or adenosine.

In a further example of the above aspects and examples, the coupling site includes a carboxyl moiety and activating includes reacting with a succinimidyl compound.

In an additional example of the above aspects and examples, the coupling site includes an amine moiety.

In another example of the above aspects and examples, the coupling site includes a hydroxyl moiety.

In a further example of the above aspects and examples, the methods further includes hybridizing a template nucleic acid to the oligonucleotide and extending the oligonucleotide. For example, the methods can further include sequencing the extended oligonucleotide.

In an additional example of the above aspects and examples, the substrate is a hydrogel network. For example, the hydrogel network is a discrete hydrogel network. In a further example, the hydrogel network includes polyacrylamide.

In another example of the above aspects and examples, exposing the substrate is performed in an emulsion. For example, the methods can further include breaking the emulsion to recover the substrates prior to washing. In another example, the method further includes enriching the substrate to separate the substrate from unamplified substrates. In an additional example, the method further includes depositing the substrate on a sequencing device. In a particular example, the method further includes sequencing the extended oligonucleotide.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A method of sequencing a nucleic acid target, the method comprising:
   applying a discrete substrate to a sequencing device, the discrete substrate conjugated to a 5' terminal end of the nucleic acid target at a coupling site of the discrete substrate, a functional moiety coupled between the 5' terminal end of the nucleic acid target and the discrete substrate, wherein the functional moiety is a dye moiety or a buffering moiety, wherein the functional moiety is attached to a modified nucleotide that includes a 7-deaza-purine base, wherein the functional moiety is attached to the 7-position of the 7-deaza-purine base;
   applying a primer complementary to a portion of the nucleic acid target;
   flowing a nucleotide into the sequencing device; and
   detecting an incorporation event associated with the nucleotide.

2. The method of claim 1, further comprising performing ion exchange on the nucleic acid target.

3. The method of claim 1, wherein the functional moiety is a dye moiety.

4. The method of claim 3, wherein the dye moiety is a rhodamine moiety.

5. The method of claim 3, wherein the dye moiety is a fluorescein moiety.

6. The method of claim 1, wherein the functional moiety is a buffering moiety.

7. The method of claim 6, wherein the buffering moiety is selected from the group consisting of morpholinoalkyl, triethanolamine, N-[tris(hydroxymethyl) methyl]-2-aminoethanesulfonic acid, 3-(N-tris[hydroxymethyl]methylamino)-2-hydroxypropanesulfonic acid, N-(2-hydroxyethyl) piperazine-N-(2-ethanesulfonic acid), N-(2-acetamido)-2-aminoethanesulfonic acid, imidazole, acetate, and any combination thereof.

8. The method of claim 1, wherein the 7-deaza-purine base include guanosine or adenosine.

9. The method of claim 1, further comprising:
   forming the nucleic acid target by hybridizing a template nucleic acid to an oligonucleotide coupled to the discrete substrate, the functional moiety coupled between the 5' terminal end of the oligonucleotide and the discrete substrate; and
   extending the oligonucleotide.

10. The method of claim 9, further comprising sequencing the extended oligonucleotide.

11. The method of claim 1, wherein the discrete substrate is a hydrogel network.

12. The method of claim 11, wherein the hydrogel network includes polyacrylamide.

* * * * *